(12) United States Patent
Nakano

(10) Patent No.: US 9,536,302 B2
(45) Date of Patent: Jan. 3, 2017

(54) IMAGE PROCESSING APPARATUS, X-RAY RADIOGRAPHIC APPARATUS, AND IMAGE PROCESSING METHOD

(71) Applicant: TOSHIBA MEDICAL SYSTEMS CORPORATION, Otawara-Shi (JP)

(72) Inventor: Fumiki Nakano, Utsunomiya (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 14/031,820

(22) Filed: Sep. 19, 2013

(65) Prior Publication Data

US 2014/0016851 A1    Jan. 16, 2014

Related U.S. Application Data

(63) Continuation of application No. PCT/JP2013/056036, filed on Mar. 5, 2013.

(30) Foreign Application Priority Data

Mar. 6, 2012  (JP) ................................ 2012-049723

(51) Int. Cl.
 *G06T 7/00*    (2006.01)
 *A61B 6/00*    (2006.01)
 *A61B 6/12*    (2006.01)

(52) U.S. Cl.
 CPC ............... *G06T 7/0012* (2013.01); *A61B 6/12* (2013.01); *A61B 6/463* (2013.01); *A61B 6/504* (2013.01); *A61B 6/5235* (2013.01); *A61B 6/5241* (2013.01); *A61B 6/4441* (2013.01);
 (Continued)

(58) Field of Classification Search
 None
 See application file for complete search history.

(56) References Cited

U.S. PATENT DOCUMENTS

| 6,782,284 B1* | 8/2004 | Subramanyan et al. ...... 600/407 |
| 2010/0073171 A1* | 3/2010 | Frinak et al. .............. 340/573.1 |
| 2011/0110496 A1* | 5/2011 | Foos et al. ................... 378/98.5 |

FOREIGN PATENT DOCUMENTS

| JP | 2003-000700 | 1/2003 |
| JP | 2011-139821 | 7/2011 |

OTHER PUBLICATIONS

Volkau, Ihar, et al. "Geometric modeling of the human normal cerebral arterial system." Medical Imaging, IEEE Transactions on 24.4 (2005): 529-539.*

(Continued)

*Primary Examiner* — Stephen R Koziol
*Assistant Examiner* — Raphael Schwartz
(74) *Attorney, Agent, or Firm* — Oblon, McClelland, Maier & Neustadt, L.L.P.

(57) ABSTRACT

An image processing apparatus has an extraction unit, a base calculation unit, a recommended-region calculation unit and a display unit. The extraction unit extracts a region including a branch artery of a subject based on volume data. The base calculation unit calculates a base of the branch artery based on the region including the branch artery. The recommended-region calculation unit calculates a recommended region for placing a balloon of a balloon catheter based on the volume data and the base. The display unit aligns and displays the recommended region on a basic image.

14 Claims, 16 Drawing Sheets

(52) U.S. Cl.
CPC ............ *A61B 6/503* (2013.01); *A61B 6/5217* (2013.01); *A61B 2090/3764* (2016.02)

(56) References Cited

OTHER PUBLICATIONS

International Search Report issued on Jun. 11, 2013 for PCT/JP2013/056036 filed on Mar. 5, 2013 with English Translation of Categories.
Kim et al.; "The Carina as a Useful Radiographic Landmark for Positioning the Intraortic Balloon Pump"; Anasthesia & Analgesia; Sep. 2007; vol. 105. No. 3, pp. 735-738.
International Preliminary Report on Patentability issued Sep. 9, 2014 in PCT/JP2013/056036 filed on Mar. 5, 2013.
Written Opinion issued Jun. 11, 2013 in PCT/JP2013/056036 filed on Mar. 5, 2013 (with English translation).

* cited by examiner

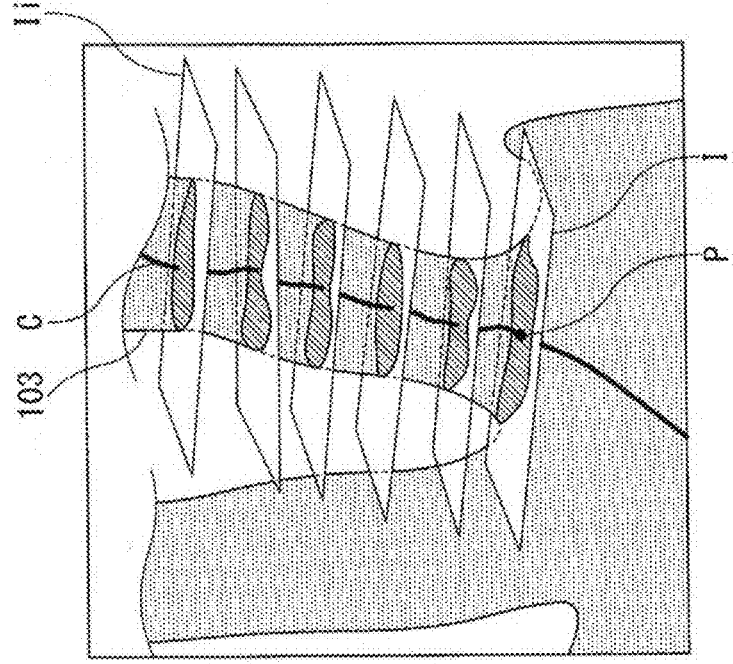
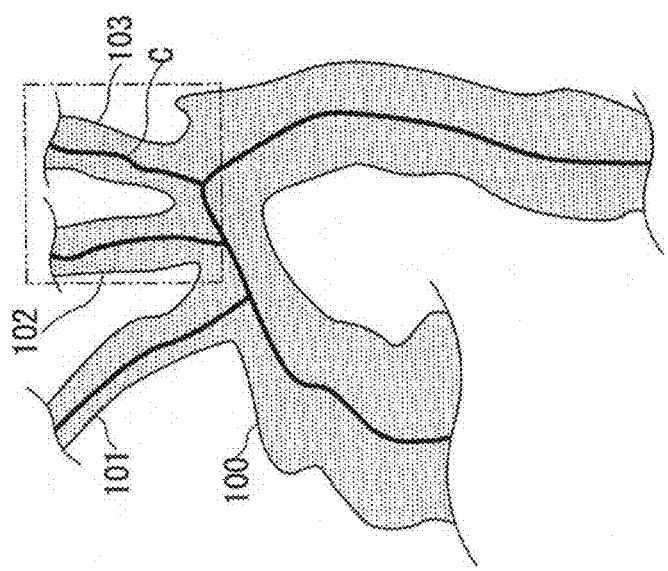
FIG. 6A
FIG. 6B

IMAGE PROCESSING APPARATUS, X-RAY RADIOGRAPHIC APPARATUS, AND IMAGE PROCESSING METHOD

CROSS-REFERENCE TO RELATED APPLICATION

This application is a Continuation Application of No. PCT/JP2013/56036, filed on Mar. 5, 2013, and the PCT application is based upon and claims the benefit of priority from Japanese Patent Application No. 2012-49723, filed on Mar. 6, 2012, the entire contents of which are incorporated herein by reference.

FIELD

The present embodiment as one aspect of the present invention relates to an image processing apparatus, an X-ray radiographic apparatus and an image processing method to perform image processing.

BACKGROUND

Conventionally, in the industrial field such as non-destructive inspections and the medical field such as medical examinations, an X-ray radiographic apparatus is used widely, where the X-ray radiographic apparatus irradiates a test object or a subject with radiation (typically X-rays), detects an intensity distribution of the radiation transmitted through the test object or the subject, and thereby obtains an image of the test object or the subject.

Intra-aortic balloon pumping (IABP) is used under conditions of decreased cardiac output and lowered blood pressure resulting from a significant decline in cardiac function. Application of IABP to various cases including valve replacement procedures, coronary artery disease surgeries, severe angina, and reconstructive coronary artery surgeries has been reported recently. The IABP is a simple and safe technique, and is thus expected to be applied to a wide range of cases in future.

If an IABP balloon catheter is inserted in the aorta of a patient and the balloon is inflated and deflated in synchronization with the heartbeat, IABP is effective in increasing myocardial oxygen supply and decreasing myocardial oxygen consumption. When IABP is used, the balloon assists the heart, reducing the load on the heart, and thereby making it possible to maintain blood flow through the coronary arteries and blood circulation through the whole body. The IABP, if performed until the cardiac function is restored, can reduce the possibility of the patient falling into a serious condition.

According to conventional techniques, a recommended placement position of the balloon of the IABP balloon catheter is a position 1 to 2 cm away from a base of the left subclavian artery (LSCA) in a direction of the feet. However, LSCA position serving as a reference for the placement position of the balloon is not clearly visible on X-ray images.

In actual clinical situations, a method is adopted which indirectly places the balloon of the IABP balloon catheter at a recommended position with reference to another landmark (the carina, aortic knob, or the like) visible on X-ray images. However, depending on the patient, the balloon is brought into contact with or too close to the LSCA, failing to provide an intended effect.

BRIEF DESCRIPTION OF THE DRAWINGS

In accompanying drawings,

FIGS. 6A and 6B are diagrams for explaining a method for calculating a base of a LSCA;

DETAILED DESCRIPTION

An image processing apparatus, an X-ray radiographic apparatus and an image processing method according to the present embodiment will be described with reference to an attached drawing.

To solve the above-described problems, the present embodiments provide the image processing apparatus including: an extraction unit configured to extract a region including a branch artery of a subject based on volume data; a base calculation unit configured to calculate a base of the branch artery based on the region including the branch artery; a recommended-region calculation unit configured to calculate a recommended region for placing a balloon of a balloon catheter based on the volume data and the base; and a display unit configured to align and display the recommended region on a basic image.

To solve the above-described problems, the present embodiments provide the X-ray radiographic apparatus including: an extraction unit configured to extract a region including a branch artery of a subject based on volume data; a base calculation unit configured to calculate a base of the branch artery based on the region including the branch artery; a recommended-region calculation unit configured to calculate a recommended region for placing a balloon of a balloon catheter based on the volume data and the base; an X-ray irradiation device configured to emit X-rays; an X-ray detection device placed facing the X-ray irradiation device and configured to detect the X-rays; an execution unit configured to control operation of the X-ray irradiation device and the X-ray detection device and perform X-ray radiography of the region including the branch artery; and a display unit configured to align and display the region including the branch artery, the recommended region, and a balloon image on an X-ray image collected by the execution unit, the balloon image representing the balloon as inflated.

To solve the above-described problems, the present embodiments provide the image processing method including: acquiring volume data from a storage device; extracting a region including a branch artery of a subject based on the volume data; calculating a base of the branch artery based on the region including the branch artery; calculating a recommended region for placing a balloon of a balloon catheter based on the volume data and the base; and aligning and displaying the recommended region on a basic image.

First Embodiment

Figure 1:
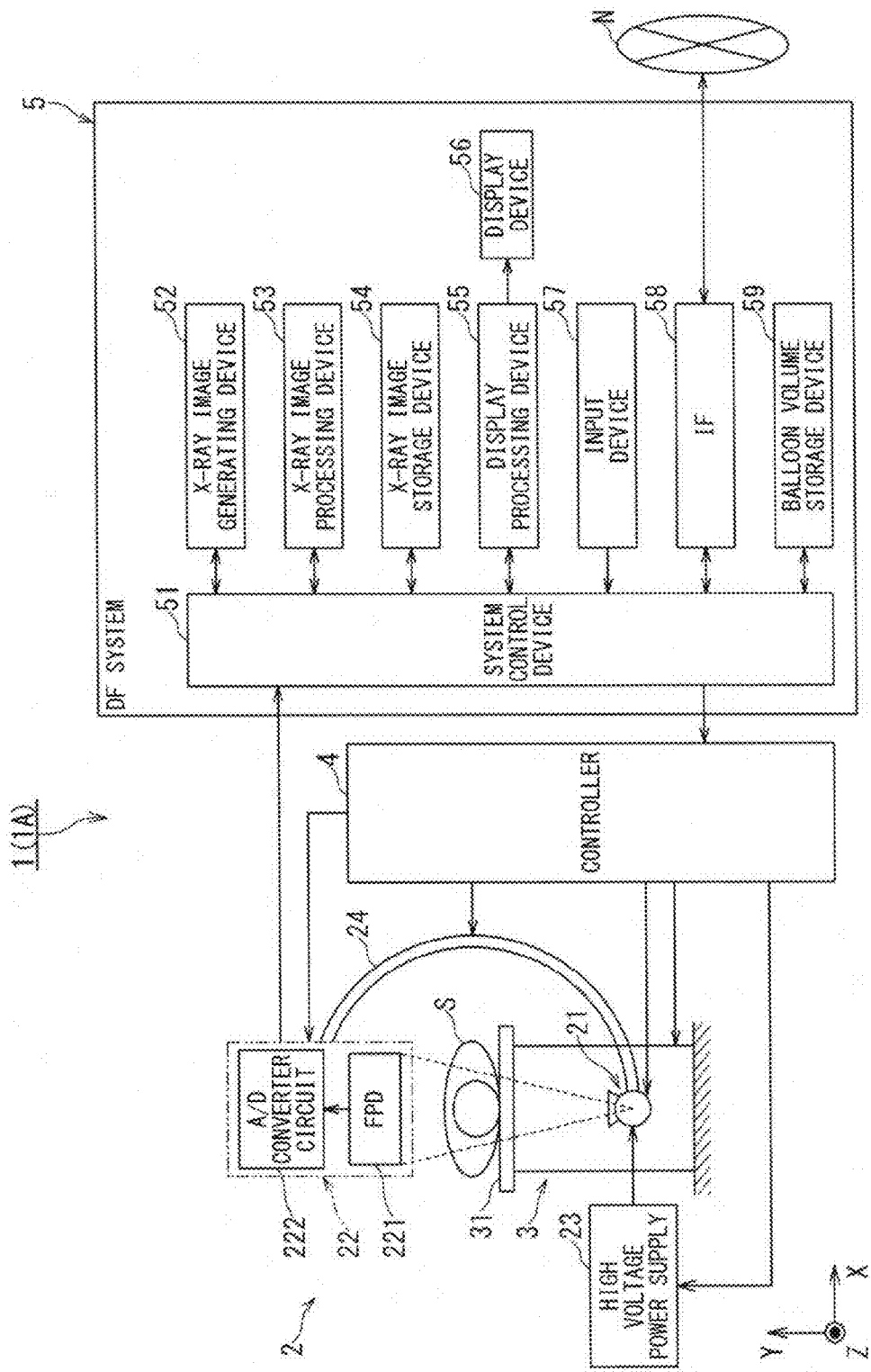
FIG. 1 is a schematic diagram showing a configuration of an X-ray radiographic apparatus according to a first embodiment.
Figure 2:
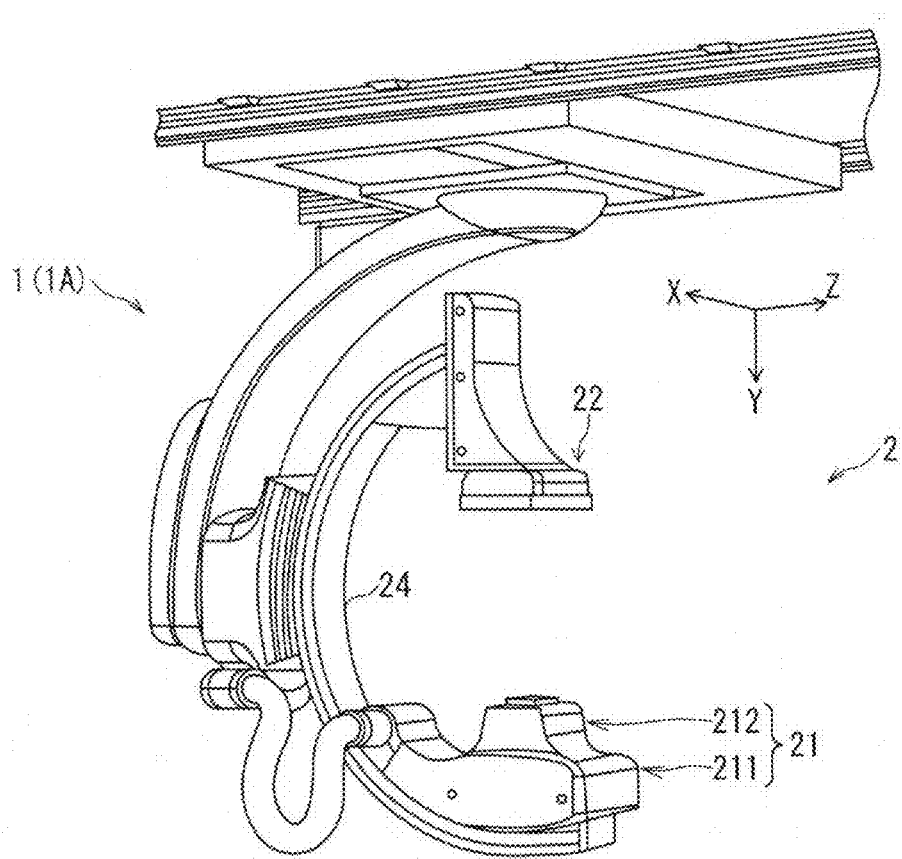
FIG. 2 is a perspective view showing an external configuration of the X-ray radiographic apparatus according to the first embodiment when the X-ray radiographic apparatus is equipped with an overhead traveling C arm.

FIG. 1 is a schematic diagram showing a configuration of an X-ray radiographic apparatus according to a first embodiment. FIG. 2 is a perspective view showing an external configuration of the X-ray radiographic apparatus according to the first embodiment when the X-ray radiographic apparatus is equipped with an overhead traveling C arm.

FIGS. 1 and 2 show the X-ray radiographic apparatus 1 according to the first embodiment, where the X-ray radiographic apparatus 1 is adapted to perform IABP (intra-aortic balloon pumping). The X-ray radiographic apparatus 1 largely includes a gantry system 2, a bed system 3, a controller 4, and a DF (digital fluorography) system 5. The gantry system 2, bed system 3, and controller 4 are generally installed in a surgical operating room (examination/treatment room) while the DF system 5 is installed in a control room located next to the surgical operating room.

The gantry system 2 includes an X-ray irradiation device 21, an X-ray detection device 22, a high voltage power supply 23, and a C arm 24.

The X-ray irradiation device 21 is installed at one end of the C arm 24. The X-ray irradiation device 21 is configured to be able to move forward and backward under the control of the controller 4. The X-ray irradiation device 21 includes an X-ray tube (an X-ray source) 211 and a movable beam limiting device 212 as shown in FIG. 2.

The X-ray tube 211 is supplied with high voltage power from the high voltage power supply 23 and generates X-rays according to conditions of the high voltage power.

The movable beam limiting device 212 movably supports aperture blades made of a material which blocks X-rays at an X-ray irradiation opening of the X-ray tube 211. A radiation quality adjustment filter (not shown) adapted to adjust radiation quality of the X-rays generated by the X-ray tube 211 may be provided on the front of the X-ray tube 211.

The X-ray detection device 22 is installed at another end of the C arm 24, facing the X-ray irradiation device 21. The X-ray detection device 22 is configured to be able to move forward and backward under the control of the controller 4.

The X-ray detection device 22 includes an FPD (flat panel detector) 221 and an A/D (analog to digital) converter circuit 222.

The FPD 221 includes plural detecting elements arranged two-dimensionally. A scanning line and a signal line are disposed at right angles to each other between each pair of the detecting elements of FPD 221. Note that a grid (not shown) may be provided on the front of FPD 221. To absorb scattered radiation incident on the FPD 221 and improve contrast of X-ray images, the grid includes grid plates made of lead or the like with high X-ray absorption and aluminum, wood, or the like transparent to X-rays, with the grid plates and aluminum or wood being arranged alternately.

The A/D converter circuit 222 converts projection data of a time-series analog signal (video signal) outputted from the FPD 221 into a digital signal, and outputs the digital signal to the DF system 5.

Note that the X-ray detection device 22 may be an I.I. (image intensifier)-TV system. The I.I.-TV system converts X-rays transmitted through a subject S and X-rays entering directly, into visible light and doubles luminance in the process of light-electron-light conversion, thereby forming projection data of high sensitivity. Then, the I.I.-TV system converts the optical projection data into an electrical signal using a CCD (charge coupled device) image sensor.

The high voltage power supply 23 is capable of supplying high voltage power to the X-ray tube 211 of the X-ray irradiation device 21 under the control of the controller 4.

The C arm 24 places the X-ray irradiation device 21 and X-ray detection device 22 on opposite sides of the subject S, facing each other. Under the control of the controller 4, the C arm 24 causes the X-ray irradiation device 21 and X-ray detection device 22 to make arcing motions as an integral unit along an arc direction of the C arm 24.

Being supported on a floor surface, the bed system 3 supports a table top 31. Under the control of the controller 4, the bed system 3 causes the table top 31 to make sliding motions (in X- and Z-axis directions), up-and-down motions (in a Y-axis direction), and rolling motions. The subject S can be placed on the table top 31. Although the gantry system 2 is described by assuming that the X-ray irradiation device 21 is an under-tube type located below the table top 31, the gantry system 2 is also applicable when the X-ray irradiation device 21 is an over-tube type located above the table top 31.

The controller 4 includes a CPU (central processing unit) and a memory (neither is shown). Under the control of the DF system 5, the controller 4 controls driving of the X-ray irradiation device 21, X-ray detection device 22, and C arm 24 on the gantry system 2 as well as driving of the bed system 3, for the purpose of alignment. Also, under the control of the DF system 5, the controller 4 controls operation of the X-ray irradiation device 21, X-ray detection device 22, and high voltage power supply 23, for surgery-related X-ray radiography (radioscopy).

The DF system 5 is constructed based on a computer and is adapted to perform operation control of the entire X-ray radiographic apparatus 1 as well as to perform image processing of plural X-ray images (X-ray image data) acquired by the gantry system 2. The DF system 5 includes a system control device 51, an X-ray image generating device 52, an X-ray image processing device 53, an X-ray image storage device 54, a display processing device 55, a display device 56, an input device 57, an IF (interface) 58, and a balloon volume storage device 59.

The system control device 51 includes a CPU and memory (neither is shown). The system control device 51 controls the controller 4 as well as the components 52 to 55 and 57 to 59.

Under the control of the system control device 51, the X-ray image generating device 52 applies a logarithmic transformation process (LOG process) to the projection data outputted from the A/D converter circuit 222 on the gantry system 2, performs an addition process as required, and thereby generates X-ray images.

Under the control of the system control device 51, the X-ray image processing device 53 applies image processing to the X-ray images generated by the X-ray image generating device 52. Examples of image processing include expansion, gradation processing, and spatial filtering of data; minimum value and maximum value tracing of data accumulated in time sequence; and addition intended to remove noise. The data subjected to image processing by the X-ray image processing device 53 is outputted to the display device 56 through the display processing device 55 as well as stored in a storage device such as the X-ray image storage device 54.

Under the control of the system control device 51, the display processing device 55 combines the X-ray images processed by X-ray image processing device 53 and composite images generated by the system control device 51 with text information and scales of various parameters and outputs resulting data to the display device 56 as a video signal.

The display device 56 displays the data outputted from the display processing device 55 with the text information and scales of various parameters.

The input device 57 includes a keyboard and mouse which can be manipulated by an operator such as a surgeon, and an input signal corresponding to a manipulation is sent to the system control device 51.

The IF 58 is made up of connectors compliant with parallel connection specifications and serial connection specifications. The IF 58 has a function to connect to a network N through communications control in accordance with appropriate standard and thereby allows the DF system 5 to be connected to the network N.

The balloon volume storage device 59 stores a balloon volume (balloon volume data) which simulates a shape of an inflated balloon of an IABP balloon catheter (hereinafter referred to simply as a "balloon catheter").

Figure 3:
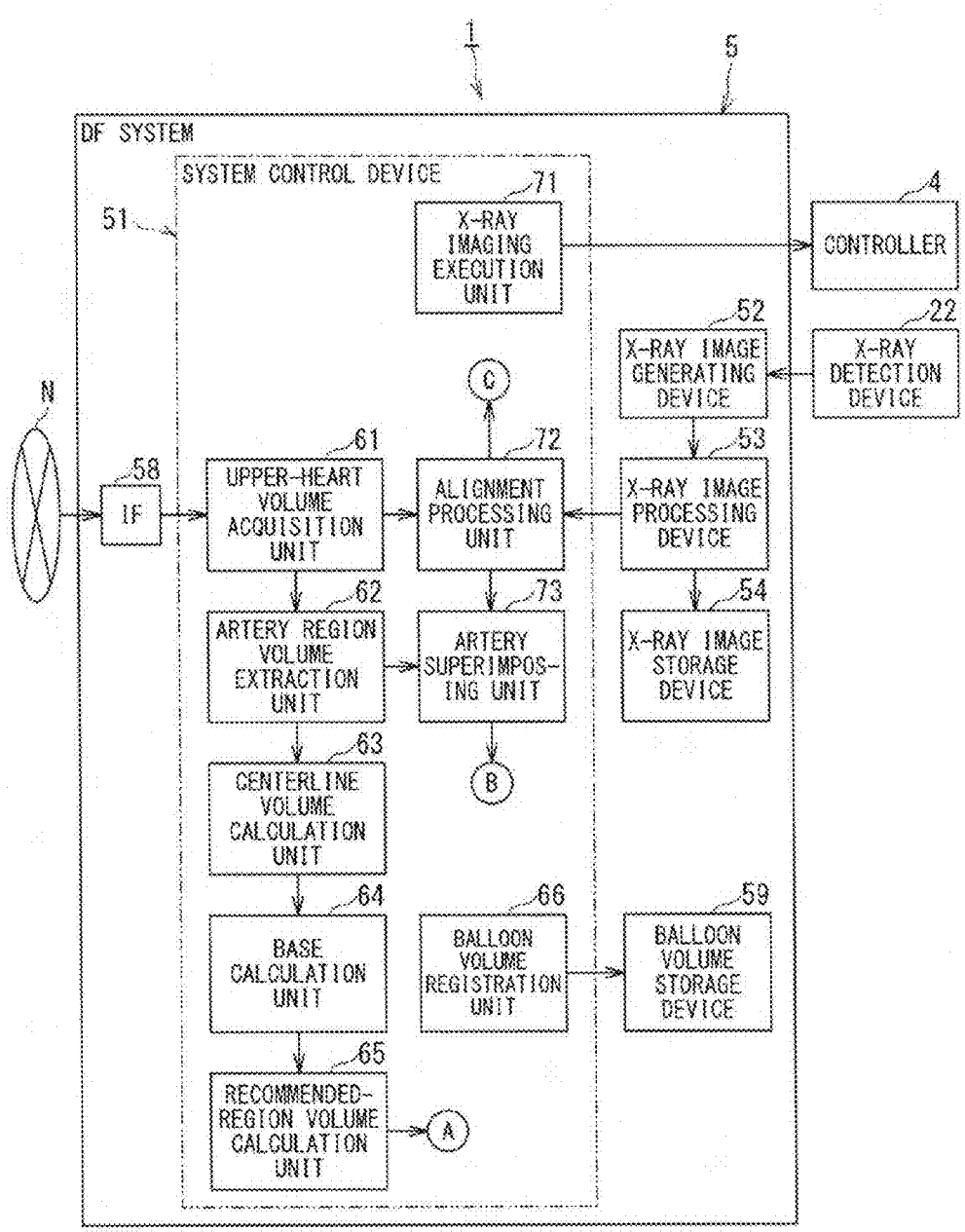
FIG. 3 is a block diagram showing functions of the X-ray radiographic apparatus according to the first embodiment.
Figure 4:
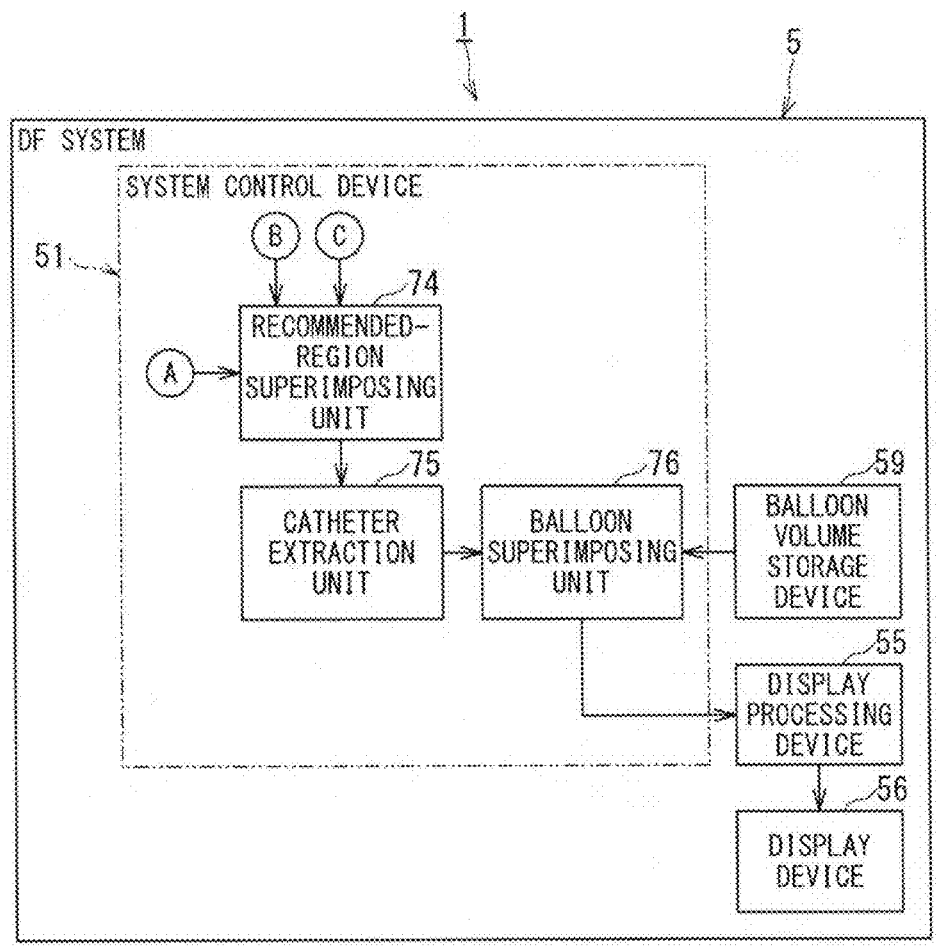
FIG. 4 is a block diagram showing functions of the X-ray radiographic apparatus according to the first embodiment.

FIGS. 3 and 4 are block diagrams showing functions of the X-ray radiographic apparatus 1 according to the first embodiment.

As the system control device 51 shown in FIG. 1 executes a program, the X-ray radiographic apparatus 1 functions as an upper-heart volume acquisition unit 61, an artery region volume extraction unit 62, a centerline volume calculation unit 63, a base calculation unit 64, a recommended-region volume calculation unit 65, a balloon volume registration unit 66, an X-ray imaging execution unit 71, an alignment processing unit 72, an artery superimposing unit 73, a recommended-region superimposing unit 74, a catheter extraction unit 75, and a balloon superimposing unit 76, as shown in FIGS. 3 and 4. Note that although it has been stated that the components 61 to 66 and 71 to 76 making up the X-ray radiographic apparatus 1 function when a program is executed, this is not restrictive. All or part of the components 61 to 66 and 71 to 76 making up the X-ray radiographic apparatus 1 may be provided as hardware on the X-ray radiographic apparatus 1.

Note that whereas the components 61 to 66 making up the X-ray radiographic apparatus 1 function in advance before surgery-related X-ray radiography (radioscopy) is done, the components 71 to 76 making up the X-ray radiographic apparatus 1 function during surgery-related X-ray radiography (radioscopy).

Referring to FIG. 3, the heart volume acquisition unit 61 has a function to acquire an upper-heart volume (upper-heart volume data) from the network N via the IF 58, where the upper-heart volume concerns a region including the aortic arch of the aorta in the upper part of the heart of the subject S and branch arteries (brachiocephalic trunk (BCA), left common carotid artery (LCA), and left subclavian artery (LSCA)) branching off from the aortic arch. For example, the upper-heart volume acquisition unit 61 acquires the upper-heart volume generated by MR angiography (MRA) and CT angiography (CTA).

The artery region volume extraction unit 62 has a function to extract the artery region volume (artery region volume data) including an aorta region and branch artery (BCA, LCA, and LSCA) region based on the upper-heart volume acquired by the upper-heart volume acquisition unit 61. The artery region volume extraction unit 62 extracts the artery region volume based on a well-known technique or on a region entered, via the input device 57 (shown in FIG. 1), on an image which is based on the upper-heart volume displayed on the display device 56 (shown in FIG. 4). Examples of available conventional techniques include a segmentation process.

Figure 5:
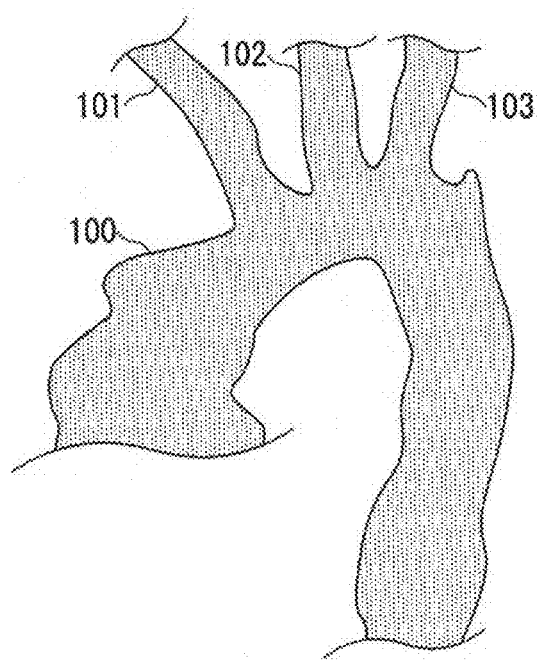
FIG. 5 is a diagram showing an example of a upper-heart volume.

FIG. 5 is a diagram showing an example of the upper-heart volume.

FIG. 5 is a diagram two-dimensionally showing an artery region volume. As shown in FIG. 5, the artery region volume includes an aortic arch region 100 of the aorta in the upper part of the heart as well as a BCA region 101, LCA region 102, and LSCA region 103, which are branch artery regions branching off from the aortic arch region 100.

Returning to FIG. 3, the centerline volume calculation unit 63 has a function to calculate a centerline volume (centerline volume data) of a centerline in the artery region based on the artery region volume extracted by the artery region volume extraction unit 62. The centerline volume calculation unit 63 calculates the centerline volume based on a well-known technique or on a wire entered, via the input device 57 (shown in FIG. 1), on an image which is based on the artery region volume and is displayed on the display device 56 (shown in FIG. 4).

The base calculation unit 64 has a function to calculate bases of branch arteries based on the artery region volume extracted by the artery region volume extraction unit 62. The base calculation unit 64 calculates the base of at least one of the BCA, LCA, and LSCA, which are branch arteries. In the following description, it is assumed that the base calculation unit 64 calculates the bases of the branch arteries LSCA.

The base calculation unit 64 calculates the base (base data) of the branch artery LSCA based on the artery region volume extracted by the artery region volume extraction unit 62 and the centerline volume calculated by the centerline volume calculation unit 63. In so doing, the base calculation unit 64 generates plural cross-centerline sections (cross-centerline section data) (orthogonal to the centerline) along the centerline of the LSCA region based on the artery region volume. Then, the base calculation unit 64 extracts respective shapes (cross sections as well as lengths of a major axis and minor axis) of LSCA region cross sections based on the plural cross-centerline sections, selects an LSCA region cross section which maximizes an amount of increase in the shape (a ratio of the amount of increase to distances among the plural LSCA region cross sections) from the plural LSCA region cross sections, and calculates an intersection between the selected LSCA region cross section and the centerline as the base of the LSCA.

FIGS. 6A and 6B are diagrams for explaining a method for calculating the base of the LSCA.

FIG. 6A is a diagram two-dimensionally showing an artery region volume. As shown in FIG. 6A, the artery region volume includes an aortic arch region 100 in the upper part of the heart as well as the BCA region 101, LCA region 102, and LSCA region 103, which are branch artery regions branching off from the aortic arch region 100.

Also, FIG. 6A shows a centerline C based on a branch artery region volume. FIG. 6B is an enlarged view of a portion including the LSCA region 103 of FIG. 6A.

As shown in FIG. 6B, plural cross-centerline sections Ii (i=1, 2, . . . ) are generated at positions of respective points on the centerline of the LSCA region 103. Based on the plural cross-centerline sections Ii, the shapes of the respective LSCA region cross sections are acquired. A cross-centerline section I which corresponds to the LSCA region cross section whose shape has a maximum amount of increase is extracted from the plural cross-centerline sections Ii. Then, an intersection between the LSCA region cross section of the cross-centerline section I and the centerline C are calculated as a LSCA base P.

Returning to FIG. 3, the base calculation unit 64 can calculate the base of the LSCA as a branch artery without using the centerline volume, based on the artery region volume extracted by the artery region volume extraction unit 62. For example, the base calculation unit 64 calculates, as the LSCA base, a center of gravity position of the LSCA region having a closed curve and located in the cross section which is at right angles to the body axis of the subject S and is closest to the feet.

The recommended-region volume calculation unit 65 has a function to calculate a recommended-region volume (recommended-region volume data) of the balloon placement for the balloon catheter based on the upper-heart volume acquired by the upper-heart volume acquisition unit 61 as well as on the LSCA base calculated by the base calculation unit 64. Based on the upper-heart volume, the recommended-region volume calculation unit 65 calculates an LSCA base plane (LSCA base plane data) which is perpendicular to the body axis direction (Z-axis direction) of the subject S and which passes through the LSCA base. Then, the recommended-region volume calculation unit 65 calculates, as the recommended-region volume, a region surrounded by a first plane (first plane data) 1 cm away from the LSCA base plane in the direction of the feet and a second plane (second plane data) 2 cm away from the LSCA base plane in the direction of the feet.

Figure 7:
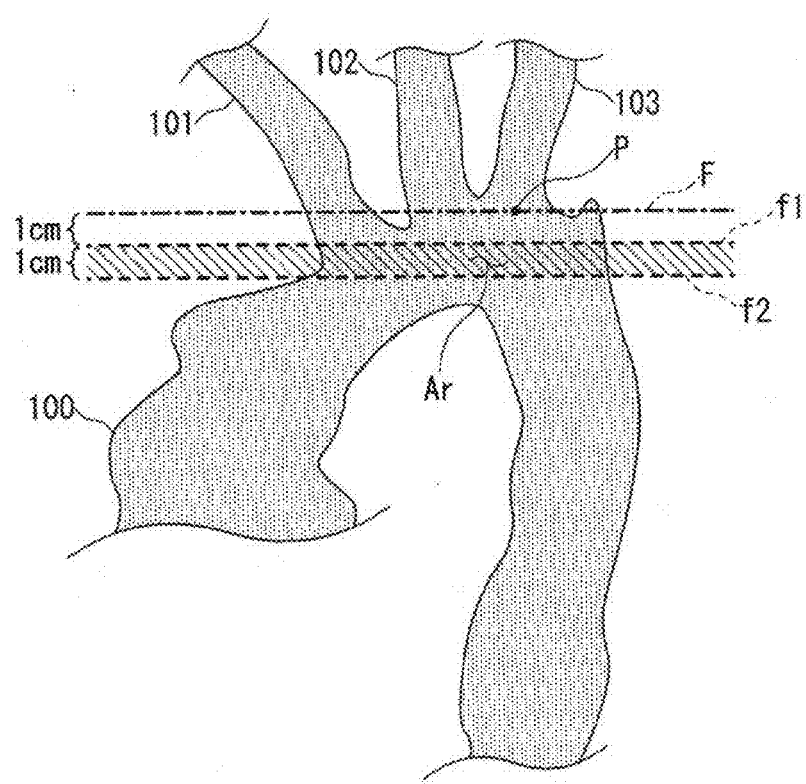
FIG. 7 is a diagram for explaining a method for calculating a recommended-region volume.

FIG. 7 is a diagram for explaining a method for calculating a recommended-region volume.

FIG. 7 is a diagram two-dimensionally showing an artery region volume. As shown in FIG. 7, the artery region volume includes an aortic arch region 100 in the upper part of the heart as well as the BCA region 101, LCA region 102, and LSCA region 103, which are branch artery regions branching off from the aortic arch region 100.

Also, FIG. 7 shows a LSCA base plane F which is perpendicular to the body axis direction of the subject S and passes through the LSCA base P.

As shown in FIG. 7, a first plane f1 and a second plane f2 are calculated, the first plane f1 being 1 cm away from the LSCA base plane F in the direction of the feet and the second plane f2 being 2 cm away from the LSCA base plane F in the direction of the feet. Also, a region surrounded by the first plane f1 and the second plane f2 are calculated as a recommended-region volume Ar.

When a recommended-region volume is calculated from plural bases, the recommended-region volume is calculated based on a combination of the bases. For example, when a recommended-region volume is calculated from a BCA base, the LSCA base, and an LCA base, the recommended-region volume is calculated based on the base closest to the feet out of the BCA base, LSCA base, and LCA base or calculated, based on correlations among the BCA base, LSCA base, and LCA base, such that all of the BCA base, LSCA base, and LCA base will not be blocked.

Returning to FIG. 3, the balloon volume registration unit 66 has a function to register a balloon volume (balloon volume data) in the balloon volume storage device 59, the balloon volume simulating the shape of the inflated balloon of the balloon catheter.

Figure 8:
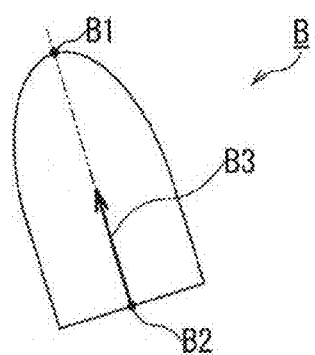
FIG. 8 is a diagram showing an example of the balloon volume.

FIG. 8 is a diagram showing an example of the balloon volume.

FIG. 8 is a diagram two-dimensionally showing a balloon volume B which simulates the shape of an inflated balloon. The balloon volume B has a forefront position (central forefront position) B1 of the inflated balloon and an orientation B3 of the inflated balloon determined as a direction from a rear end position (central rear end position) B2 to the forefront position B1.

Figure 9:
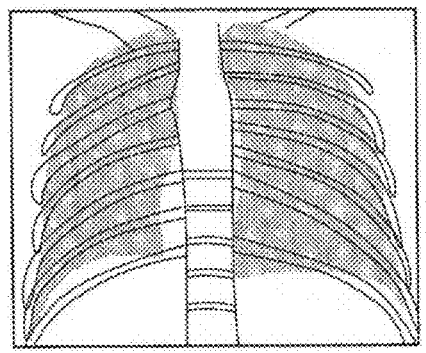
FIG. 9 is a diagram showing an example of X-ray images.

Returning to FIG. 3, the X-ray imaging execution unit 71 has a function to do alignment by driving the gantry system 2 and bed system 3 via the controller 4 in response to a command entered via the input device 57 after the subject S is put on the table top 31 of the gantry system 2. Also, the X-ray imaging execution unit 71 has a function to collect plural X-ray images (transparent images) in time sequence via the X-ray image processing device 53 by performing surgery-related X-ray radiography (radioscopy) of a region including the aortic arch of the aorta in the upper part of the heart of the subject S and the branch arteries branching off from the aortic arch by operating the X-ray irradiation device 21, X-ray detection device 22 and high voltage power supply 23. The X-ray images generated by the X-ray image processing device 53 are stored in the X-ray image storage device 54. An example of X-ray images collected by the X-ray imaging execution unit 71 is shown in FIG. 9.

The alignment processing unit 72 has a function to perform alignment of the upper-heart volume acquired by the upper-heart volume acquisition unit 61 with each of the plural X-ray images collected by the X-ray imaging execution unit 71. The alignment processing unit 72 performs an alignment process based on a well-known technique or on an X-ray image moved, via the input device 57 (shown in FIG. 1), on an image which is based on the upper-heart volume displayed on the display device 56 (shown in FIG. 4).

The artery superimposing unit 73 has a function to superimpose (combine) an artery region image (rendering image) which is based on the artery region volume extracted by the artery region volume extraction unit 62 on each of the plural X-ray images collected by the X-ray imaging execution unit 71, based on alignment results produced by the alignment processing unit 72, and thereby generate plural composite artery images (composite artery image data). Preferably the artery superimposing unit 73 generates one composite artery image per X-ray image.

Moving to FIG. 4, the recommended-region superimposing unit 74 has a function to superimpose (combine) a recommended-region image (rendering image) which is based on the recommended-region volume calculated by the recommended-region volume calculation unit 65 (shown in FIG. 3) on the plural composite artery images generated by the artery superimposing unit 73 (shown in FIG. 3), based on the alignment results produced by the alignment processing unit 72 (shown in FIG. 3), and thereby generate plural composite recommended-region images. The composite recommended-region images generated by the recommended-region superimposing unit 74 are displayed on the display device 56 through the display processing device 55. Preferably the recommended-region superimposing unit 74 generates one composite recommended-region image per X-ray image.

When a balloon catheter is inserted into the subject S to perform IABP, the catheter extraction unit 75 has a function to extract plural catheter regions of the balloon catheter based, respectively, on the plural X-ray images collected by the X-ray imaging execution unit 71 (shown in FIG. 3) and extract forefront positions and orientations of the plural catheter regions, respectively. The catheter extraction unit 75 extracts the catheter forefront positions and orientations based on a well-known technique or on an input entered, via the input device 57 (shown in FIG. 1), on an X-ray image displayed on the display device 56.

The balloon superimposing unit 76 has a function to align each of the plural catheter forefront positions and orientations extracted by the catheter extraction unit 75 with a balloon volume forefront position and orientation which simulates the shape of an inflated balloon, the balloon volume forefront position and orientation having been registered in the balloon volume storage device 59. Also, the balloon superimposing unit 76 has a function to superimpose (combine) plural balloon image (rendering image) which is based on the plural aligned balloon volumes on each of plural composite recommended-region images generated by the recommended-region superimposing unit 74 and thereby generate plural composite balloon images. Preferably the balloon superimposing unit 76 generates one composite balloon image per X-ray image.

For example, the balloon superimposing unit 76 determines the orientation of the balloon from a trajectory of the forefront position of the catheter region based on the X-ray image. The balloon superimposing unit 76 regards the direction from the forefront position of the catheter region on a past X-ray image to the forefront position of the catheter region on the current X-ray image as the current orientation of the balloon.

The balloon superimposing unit 76 causes the display processing device 55 to display the composite balloon images on the display device 56.

Figure 10:
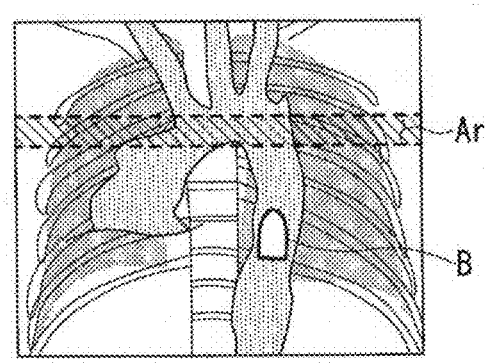
FIG. 10 is a diagram showing an example of a composite balloon image.

FIG. 10 is a diagram showing an example of the composite balloon image.

FIG. 10 shows an image including artery regions 100, 101, 102, and 103 based on an artery region volume, a recommended-region image Ar (a first straight line and a second straight line based on the first plane f1 and the second plane f2) based on a recommended-region volume, and a balloon image B at a position at a certain time point, each superimposed on an X-ray image at the time point. When the balloon catheter advances further, the balloon image B advances towards the recommended-region image Ar on the composite balloon image.

Note that the composite balloon images may be displayed together with information about the LSCA base P (shown in FIG. 6B) calculated by the base calculation unit 64 (shown in FIG. 3) and the LSCA base plane F calculated by the recommended-region volume calculation unit 65 (shown in FIG. 3).

Next, operation of the X-ray radiographic apparatus 1 according to the first embodiment will be described with reference to FIGS. 1, 11, and 12.

Figure 11:
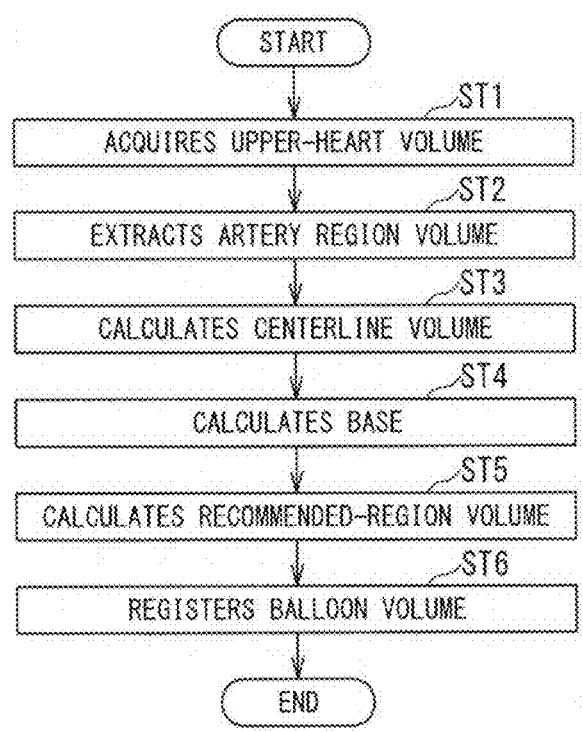
FIG. 11 is a flowchart showing an operation of the X-ray radiographic apparatus according to the first embodiment.
Figure 12:
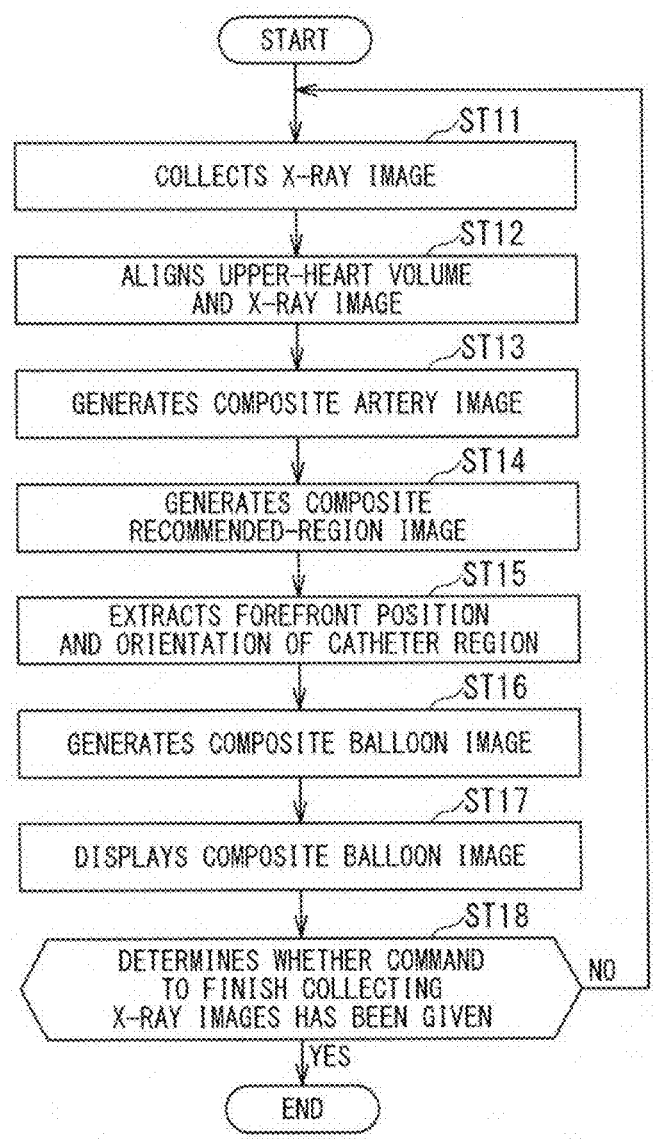
FIG. 12 is a flowchart showing an operation of the X-ray radiographic apparatus according to the first embodiment.

FIGS. 11 and 12 are flowcharts showing the operation of the X-ray radiographic apparatus 1 according to the first embodiment. Whereas Steps ST1 to ST6 shown in FIG. 11 are carried out before surgery-related X-ray radiography (radioscopy) is done, Steps ST11 to ST18 shown in FIG. 12 are carried out during the surgery-related X-ray radiography (radioscopy).

First, as shown in FIG. 11, the X-ray radiographic apparatus 1 shown in FIG. 1 acquires the upper-heart volume from the network N via the IF 58, where the upper-heart volume concerns a region including the aortic arch of the aorta in the upper part of the heart of the subject S and branch arteries (BCA, LCA, and LSCA) branching off from the aortic arch (Step ST1). For example, the X-ray radiographic apparatus 1 acquires the upper-heart volume generated by MR angiography or CT angiography.

The X-ray radiographic apparatus 1 extracts the artery region volume (shown in FIG. 5) including the aorta and branch arteries based on the upper-heart volume acquired in Step ST1 (Step ST2). The X-ray radiographic apparatus 1 calculates the centerline volume of the artery based on the artery region volume extracted by the artery region volume extraction unit 62 (Step ST3).

The X-ray radiographic apparatus 1 calculates the base of the LSCA as a branch artery as described with reference to FIGS. 6A and 6B, based on the artery region volume extracted in Step ST2 and the centerline volume calculated in Step ST3 (Step ST4). The X-ray radiographic apparatus 1 calculates the recommended-region volume of the balloon placement for the balloon catheter as described with reference to FIG. 7, based on the upper-heart volume acquired in Step ST1 and the LSCA base calculated in Step ST4 (Step ST5).

Also, the X-ray radiographic apparatus 1 registers the balloon volume (shown in FIG. 8) which simulates the shape of the inflated balloon of the balloon catheter in the balloon volume storage device 59 (Step ST6).

Next, as shown in FIG. 12, the X-ray radiographic apparatus 1 collects the X-ray image (shown in FIG. 9) by performing surgery-related X-ray radiography (radioscopy) of the region including the aortic arch of the aorta in the upper part of the heart of the subject S and the branch arteries branching off from the aortic arch (Step ST11). The X-ray radiographic apparatus 1 aligns the upper-heart volume acquired in Step ST1 (shown in FIG. 11) and the X-ray image collected in Step ST11 with each other (Step ST12).

The X-ray radiographic apparatus 1 superimposes the artery region image which is based on the artery region volume extracted in Step ST2 (shown in FIG. 11) on the X-ray image collected in Step ST11, in the upper-heart volume aligned in Step ST12, and thereby generates the composite artery image (Step ST13).

The X-ray radiographic apparatus 1 aligns and superimposes the recommended-region image which is based on the recommended-region volume calculated in Step ST5 (shown in FIG. 11) on the composite artery image generated in Step ST13, and thereby generates the composite recommended-region image (Step ST14). Next, when the balloon catheter is inserted into the subject S to perform IABP, the X-ray radiographic apparatus 1 extracts a catheter region of the balloon catheter based on the X-ray image collected in Step ST11 and extracts the forefront position and orientation of the catheter region (Step ST15).

The X-ray radiographic apparatus 1 aligns the catheter forefront position and orientation extracted in Step ST15 with the balloon volume forefront position and orientation which simulates the shape of the inflated balloon, the balloon volume forefront position and orientation having been registered in Step ST6 (shown in FIG. 11). Then, the X-ray radiographic apparatus 1 superimposes the balloon image which is based on the aligned balloon volume on the composite recommended-region image generated in Step ST14, and thereby generates the composite balloon image (shown in FIG. 10) (Step ST16). The X-ray radiographic apparatus 1 makes the display processing device 55 display the composite balloon image generated in Step ST16 on the display device 56 (Step ST17).

The X-ray radiographic apparatus 1 determines whether or not a command to finish collecting the X-ray images in Step ST11 has been given (Step ST18). If the determination in Step ST18 is YES, i.e., if it is determined that a command to finish collecting the X-ray images has been given, the X-ray radiographic apparatus 1 finishes operation.

On the other hand, if the determination in Step ST18 is NO, i.e., if it is determined that a command to finish collecting the X-ray images has not been given, the X-ray radiographic apparatus 1 collects the X-ray image in a next session (Step ST11).

The X-ray radiographic apparatus 1 according to the first embodiment can calculate a recommended region for balloon placement precisely with high accuracy and display the recommended region on a basic image. Also, the X-ray radiographic apparatus 1 according to the first embodiment can determine a recommended region for balloon placement regardless of skills of the surgeon.

Also, by displaying an estimated form of the balloon inflated at the current position of the balloon catheter on X-ray images (moving images) together with a recommended region for balloon placement, the X-ray radiographic apparatus 1 according to the first embodiment can aid the surgeon in placing the balloon of the balloon catheter during IABP.

Here, part of the functions and operation of the X-ray radiographic apparatus 1 according to the first embodiment is also applicable to an image processing apparatus.

Figure 13:
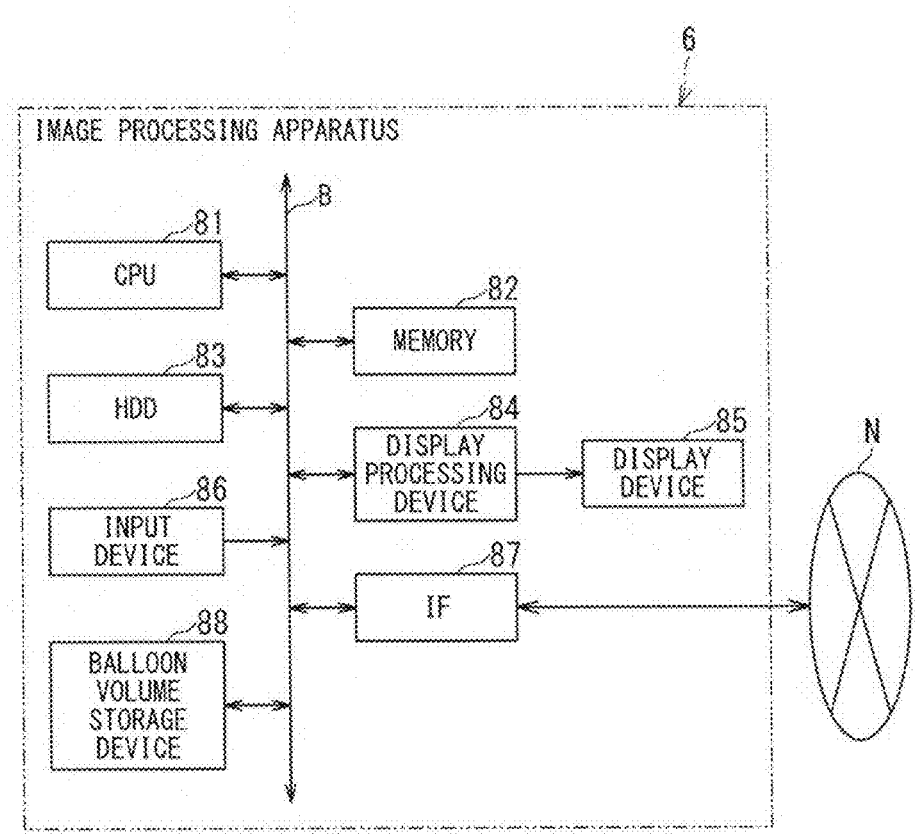
FIG. 13 is a schematic diagram showing a configuration of the image processing apparatus according to the first embodiment.

FIG. 13 is a schematic diagram showing a configuration of the image processing apparatus according to the first embodiment.

FIG. 13 shows the image processing apparatus 6 according to the first embodiment. The image processing apparatus 6 includes basic hardware largely made up of CPU 81, a memory 82, an HDD (hard disc drive) 83, a display processing device 84, a display device 85, an input device 86, an IF 87, and a balloon volume storage device 88. The CPU 81 and the hardware components which make up the image processing apparatus 6 are interconnected via a bus B serving as a common signal transmission channel.

Both CPU 81 and memory 82 are similar in configuration to the CPU and memory of the system control device 51 (shown in FIG. 1), respectively.

The HDD 83 is a storage device having a configuration in which a metal disk coated or vapor-deposited with a magnetic material is irremovably built into a reader (not shown). The HDD 83 has a function to store programs (including an OS (operating system) as well as application programs) installed on the image processing apparatus 6 and various data.

The display processing device 84 is similar in configuration to the display processing device 55 (shown in FIG. 1).

The display device 85 is similar in configuration to the display device 56 (shown in FIG. 1).

The input device 86 is similar in configuration to the input device 57 (shown in FIG. 1). An input signal corresponding to a manipulation of the input device 86 is sent to the CPU 81 through the bus B.

The IF 87, which is similar in configuration to the IF 58 (shown in FIG. 1), has a function to perform communications control according to appropriate standards and connect to the network N, thereby allowing the image processing apparatus 6 to be connected to the network N.

The balloon volume storage device 88 is similar in configuration to the balloon volume storage device 59 (shown in FIG. 1).

Figure 14:
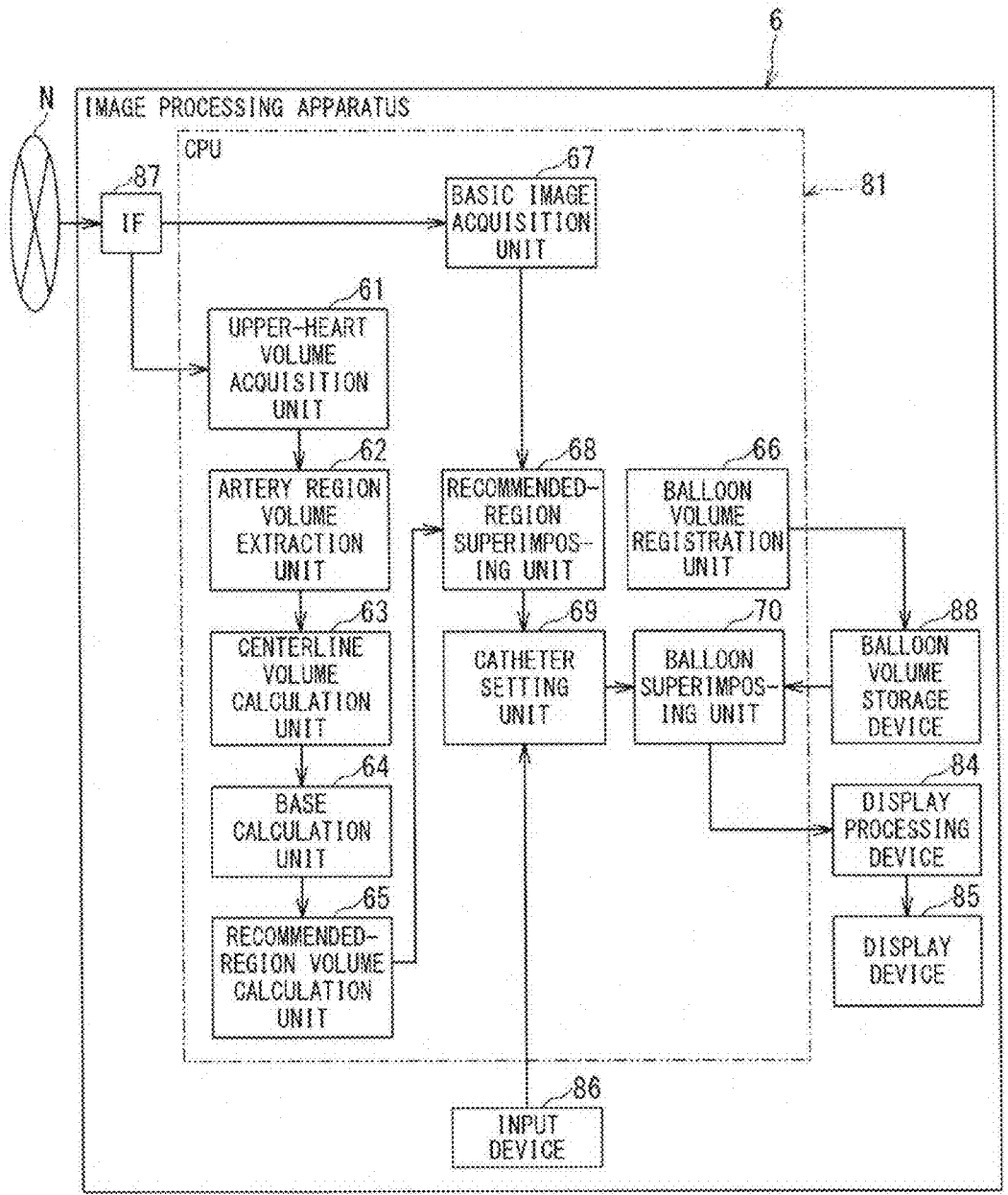
FIG. 14 is a block diagram showing functions of the image processing apparatus according to the first embodiment.

FIG. 14 is a block diagram showing functions of the image processing apparatus 6 according to the first embodiment.

As the CPU 81 shown in FIG. 13 executes a program, the image processing apparatus 6 functions as an upper-heart volume acquisition unit 61, an artery region volume extraction unit 62, a centerline volume calculation unit 63, a base calculation unit 64, a recommended-region volume calculation unit 65, a balloon volume registration unit 66, a basic image acquisition unit 67, a recommended-region superimposing unit 68, a catheter setting unit 69, and a balloon superimposing unit 70, as shown in FIG. 14. Note that although it has been stated that the components 61 to 70 making up the image processing apparatus 6 function when a program is executed, this is not restrictive. All or part of the components 61 to 70 making up the image processing apparatus 6 may be provided as hardware on the image processing apparatus 6.

Incidentally, in the image processing apparatus 6 according to the first embodiment shown in FIG. 14, the same components as those in the X-ray radiographic apparatus 1 according to the first embodiment shown in FIG. 3 are denoted by the same reference numerals as the corresponding components in the X-ray radiographic apparatus 1, and description thereof will be omitted.

The basic image acquisition unit 67 has a function to acquire an image data from the network N via the IF 87 (or from a storage device such as the HDD 83 provided in the image processing apparatus 6), where the image data concerns a region including the aortic arch of the aorta in the upper part of the heart of the subject S and branch arteries (brachiocephalic trunk (BCA), left common carotid artery (LCA), and left subclavian artery (LSCA)) branching off from the aortic arch. For example, the basic image acquisition unit 67 acquires data such as a X-ray image, an ultrasound image, a CT image, or an MRI image, which is a morphological image. Description will be given below of a case in which the basic image acquisition unit 67 acquires the X-ray image.

The recommended-region superimposing unit 68 has a function to superimpose (combine) a recommended-region image (rendering image) which is based on the recommended-region volume calculated by the recommended-region volume calculation unit 65 on the X-ray image acquired by the basic image acquisition unit 67 and thereby generate a composite recommended-region image. The composite recommended-region image generated by the recommended-region superimposing unit 68 is displayed on the display device 85 via the display processing device 84.

The catheter setting unit 69 has a function to set the distal end position and orientation of the catheter in response to a command entered, via the input device 86, on the composite recommended-region image generated by the recommended-region superimposing unit 68 (or on the basic image).

The balloon superimposing unit 70 has a function to align the distal end position and orientation of the catheter set by the catheter setting unit 69 with the distal end position and orientation of a balloon volume which simulates the shape of an inflated balloon, the distal end position and orientation of the balloon volume having been registered in the balloon volume storage device 88. Also, the balloon superimposing unit 70 has a function to superimpose (combine) a balloon image (rendering image) which is based on the aligned balloon volume on the composite recommended-region image generated by the recommended-region superimposing unit 68 and thereby generate a composite balloon image.

The balloon superimposing unit 70 makes the display processing device 84 display the composite balloon image on the display device 85.

The image processing apparatus 6 according to the first embodiment can calculate a recommended region for balloon placement precisely with high accuracy and display the recommended region on a basic image. Also, the image processing apparatus 6 according to the first embodiment can determine a recommended region for balloon placement regardless of skills of the surgeon.

Second Embodiment

Configuration of the X-ray radiographic apparatus 1A according to the second embodiment is generally the same as the configuration of the X-ray radiographic apparatus 1 according to the first embodiment shown in FIG. 1, and thus description thereof will be omitted. Also, external configuration of the X-ray radiographic apparatus 1A according to the second embodiment is the same as the external configuration of the X-ray radiographic apparatus 1 according to the first embodiment shown in FIG. 2, and thus description thereof will be omitted.

Figure 15:
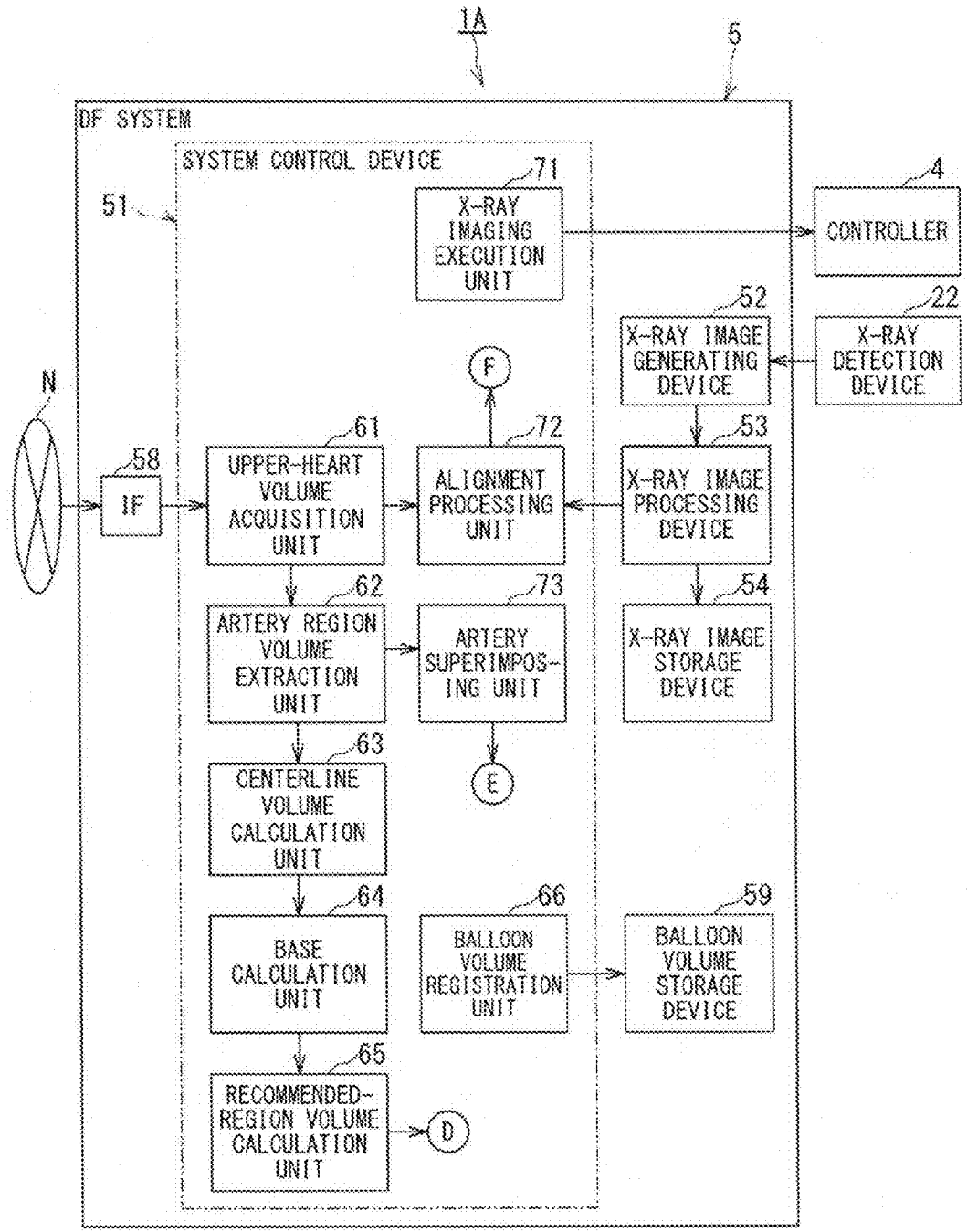
FIG. 15 is a block diagram showing functions of the X-ray radiographic apparatus according to the second embodiment.
Figure 16:
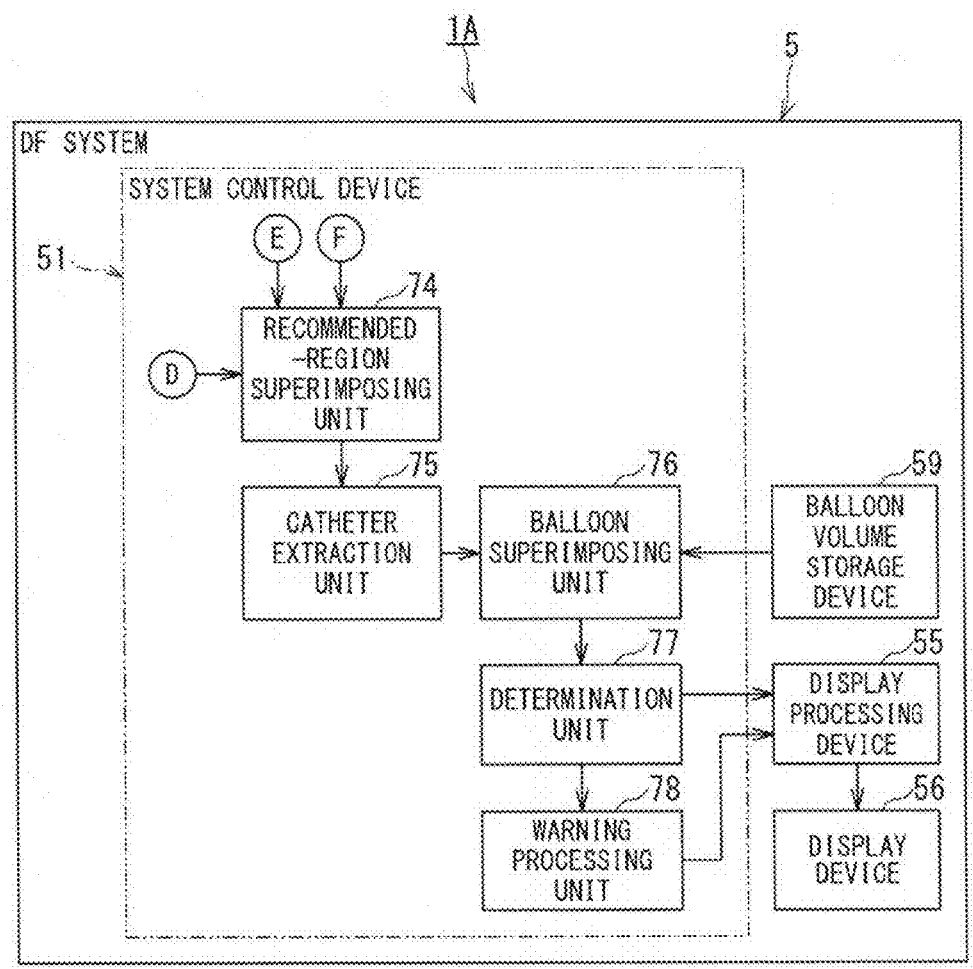
FIG. 16 is a block diagram showing functions of the X-ray radiographic apparatus according to the second embodiment.

FIGS. 15 and 16 are block diagrams showing functions of the X-ray radiographic apparatus 1A according to the second embodiment.

As the system control device 51 shown in FIG. 1 executes a program, the X-ray radiographic apparatus 1A functions as an upper-heart volume acquisition unit 61, an artery region volume extraction unit 62, a centerline volume calculation unit 63, a base calculation unit 64, a recommended-region volume calculation unit 65, a balloon volume registration unit 66, an X-ray imaging execution unit 71, an alignment processing unit 72, an artery superimposing unit 73, a recommended-region superimposing unit 74, a catheter extraction unit 75, a balloon superimposing unit 76, a determination unit 77, and a warning processing unit 78 as shown in FIGS. 15 and 16. Note that although it has been stated that the components 61 to 66 and 71 to 78 making up the X-ray radiographic apparatus 1A function when a program is executed, this is not restrictive. All or part of the components 61 to 66 and 71 to 78 making up the X-ray radiographic apparatus 1A may be provided as hardware on the X-ray radiographic apparatus 1A.

Incidentally, in the X-ray radiographic apparatus 1A according to the second embodiment shown in FIGS. 15 and 16, the same components as those in the X-ray radiographic apparatus 1 according to the first embodiment shown in FIGS. 3 and 4 are denoted by the same reference numerals as the corresponding components in the X-ray radiographic apparatus 1, and description thereof will be omitted.

Referring to FIG. 16, the determination unit 77 has a function to determine whether or not the plural catheter forefront positions of the balloon catheter on each of the plural composite balloon images generated by the balloon superimposing unit 76 goes beyond a recommended region. When it is determined that the catheter forefront position does not go beyond the recommended region, the determination unit 77 makes the display processing device 55 display the appropriate composite balloon image of these generated by the balloon superimposing unit 76 on the display device 56.

The warning processing unit 78 has a function to mark the appropriate composite balloon image generated by the balloon superimposing unit 76 for warning when it is determined by the determination unit 77 that the catheter forefront position goes beyond the recommended region. The balloon superimposing unit 76 makes the display processing device 55 display the appropriate composite balloon image marked for warning on the display device 56.

Figure 17A:
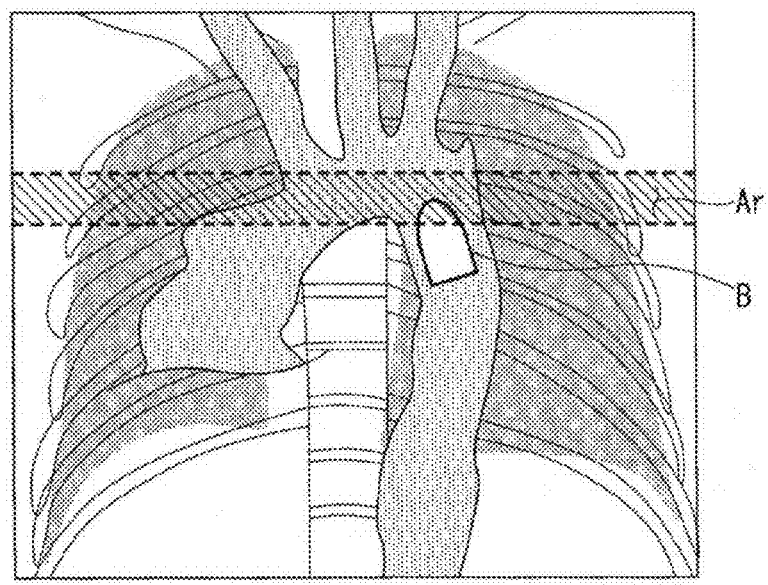
FIGS. 17A and 17B are diagrams for explaining warning status.
Figure 17B:
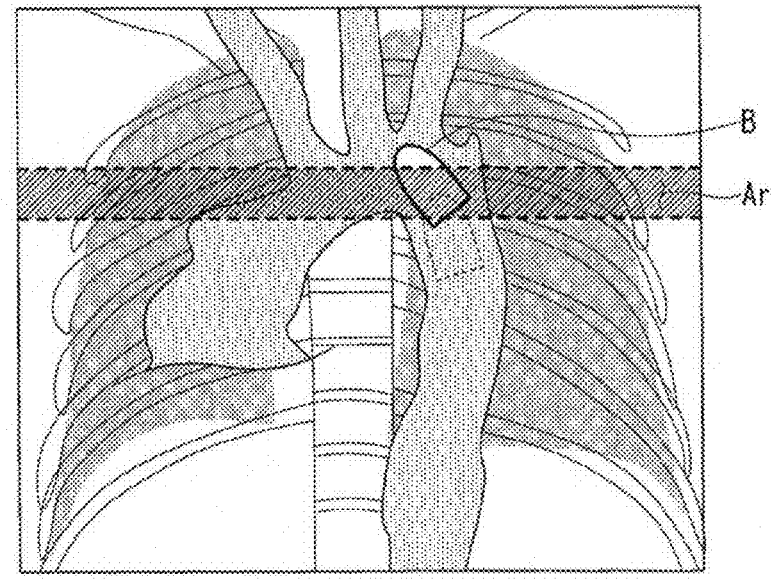

FIGS. 17A and 17B are diagrams for explaining warning status.

FIG. 17A shows an image including the artery regions 100, 101, 102, and 103 based on an artery region volume, the recommended-region image Ar based on a recommended-region volume, and the balloon image B at the position at a time point after the time point shown in FIG. 10, each superimposed on an X-ray image at the time point. Because it is determined that the catheter forefront position does not go beyond the recommended region at the time point shown in FIG. 17A, the appropriate composite balloon image is not marked for warning.

On the other hand, FIG. 17B shows an image including the artery regions 100, 101, 102, and 103 based on an artery region volume, the recommended-region image Ar based on a recommended-region volume, and the balloon image B at the position at a time point after the time point shown in FIG. 17A, each superimposed on an X-ray image at the time point. Because it is determined that the catheter forefront position goes beyond the recommended region at the time point shown in FIG. 17B, the appropriate composite balloon image is marked for warning. For example, the recommended-region image Ar is flashed or a form of display such as colors is changed.

Next, operation of the X-ray radiographic apparatus 1A according to the second embodiment will be described with reference to FIGS. 1 and 18.

Figure 18:
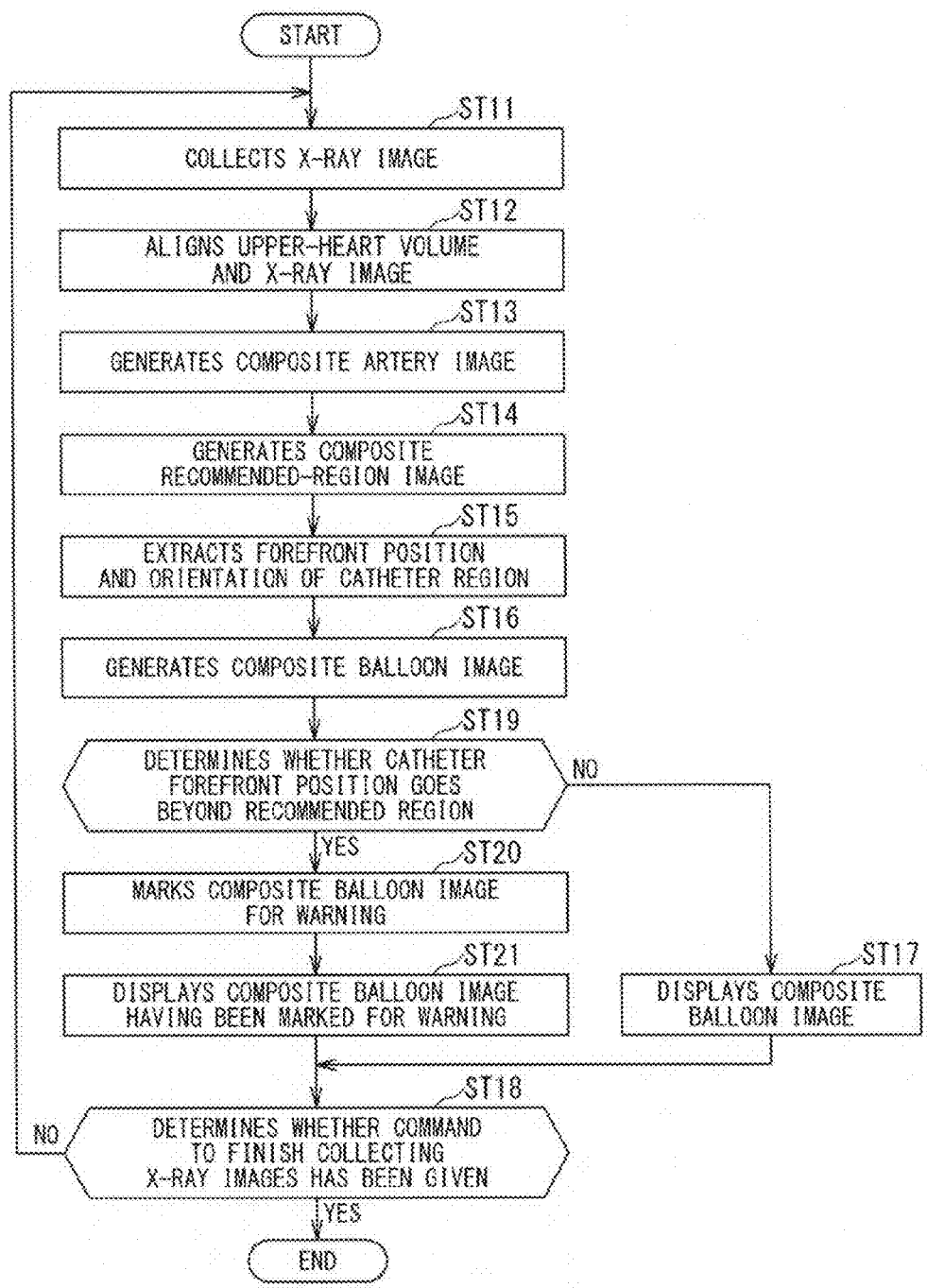
FIG. 18 is a flowchart showing the operation of the X-ray radiographic apparatus 1A according to the second embodiment.

FIG. 18 is a flowchart showing the operation of the X-ray radiographic apparatus 1A according to the second embodiment.

Steps ST11 to ST21 shown in FIG. 18 are carried out during surgery-related X-ray radiography (radioscopy). On the other hand, steps before the surgery-related X-ray radiography are similar to Steps ST1 to ST6 shown in FIG. 11, and thus description thereof will be omitted. In the flowchart shown in FIG. 18, the same steps as those in the flowchart shown in FIG. 12 are denoted by the same step numbers as the corresponding steps in FIG. 12, and description thereof will be omitted.

The X-ray radiographic apparatus 1A shown in FIG. 1 determines whether or not the catheter forefront position of the balloon catheter on the composite balloon image generated in Step ST16 goes beyond a recommended region (Step ST19). If the determination in Step ST19 is YES, i.e., if it is determined that the catheter forefront position on the composite balloon image goes beyond the recommended region, the X-ray radiographic apparatus 1A marks the appropriate composite balloon image for warning (Step ST20). Then, the X-ray radiographic apparatus 1A makes the display processing device 55 display the composite balloon image (FIG. 17B) on the display device 56 (Step ST21), the composite balloon image having been generated in Step ST20 and marked for warning.

On the other hand, if the determination in Step ST19 is NO, i.e., if it is determined that the catheter forefront position on the composite balloon image does not go beyond the recommended region, the X-ray radiographic apparatus 1A makes the display processing device 55 display the composite balloon image generated in Step ST16 on the display device 56 (Step ST17).

The X-ray radiographic apparatus 1A according to the second embodiment can calculate a recommended region for balloon placement precisely with high accuracy and display the recommended region on a basic image. Also, the X-ray radiographic apparatus 1A according to the second embodiment can determine a recommended region for balloon placement regardless of skills of the surgeon.

Further, by displaying an estimated form of the balloon inflated at the current position of the balloon catheter on X-ray images (moving images) together with a recommended region for balloon placement, the X-ray radiographic apparatus 1A according to the second embodiment can aid the surgeon in placing the balloon of the balloon catheter during IABP.

Also, since a warning is issued on X-ray images (moving images) if the current position of the balloon catheter goes beyond the recommended region, the X-ray radiographic apparatus 1A according to the second embodiment can aid the surgeon in placing the balloon of the balloon catheter during IABP.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An image processing apparatus, comprising processing circuitry, wherein the processing circuitry is configured to:
   extract a region including multiple branch arteries of a body based on volume data;
   calculate centerlines of the corresponding branch arteries based on the region;
   generate cross-centerline sections orthogonal to each of the centerlines;
   extract sectional shapes of each of the branch arteries based on the cross-centerline sections;
   extract a sectional shape that has a maximum amount of increase from the sectional shapes of each of the branch arteries;
   calculate an intersection between the extracted sectional shape and the centerline as a base of each of the branch arteries, and calculate multiple bases of the corresponding branch arteries;
   calculate a base plane based on a base closest to feet of the body out of the multiple bases;
   calculate, based on the volume data, two planes each being parallel to the base plane;
   calculate, based on the calculated two planes, a recommended region between the two planes for placing a balloon of a balloon catheter; and
   align and display the calculated recommended region on each of a plurality of X-ray images displayed as moving images.

2. The image processing apparatus according to claim 1, wherein the processing circuitry is configured to align and display a balloon image on a basic image, the balloon image representing the balloon as inflated.

3. The image processing apparatus according to claim 2, wherein the processing circuitry is configured to align the balloon image of the inflated balloon with the region including the branch artery.

4. The image processing apparatus according to claim 3, wherein the processing circuitry is configured to display a forefront position of the balloon and orientation of the balloon so as to match a forefront position and an orientation to be set actually, the forefront position of the balloon being based on a balloon volume and the orientation of the balloon being defined as a direction from a rear end position to the forefront position.

5. The image processing apparatus according to claim 1, wherein the processing circuitry is configured to
   calculate the base based on the region including the branch artery as well as on the centerline.

6. The image processing apparatus according to claim 1, wherein the processing circuitry is configured to:
   calculate the base of at least one of a brachiocephalic trunk, a left common carotid artery, and a left subclavian artery as the base of the branch artery; and
   calculate the recommended region based on the volume data and on the base of at least one of the branch arteries.

7. The image processing apparatus according to claim 1, wherein the processing circuitry is configured to display the recommended region on an X-ray image as a basic image.

8. An X-ray radiographic apparatus, comprising:
   an X-ray irradiation device configured to emit X-rays;
   an X-ray detection device placed facing the X-ray irradiation device and configured to detect the X-rays; and
   processing circuitry configured to:
      extract a region including a branch artery of a body based on volume data;
      calculate centerlines of the corresponding branch arteries based on the region;
      generate cross-centerline sections orthogonal to each of the centerlines;
      extract sectional shapes of each of the branch arteries based on the cross-centerline sections;
      extract a sectional shape that has a maximum amount of increase from the sectional shapes of each of the branch arteries;
      calculate an intersection between the extracted sectional shape and the centerline as a base of each of the branch arteries, and calculate multiple bases of the corresponding branch arteries;
      calculate a base plane based on a base closest to feet of the body out of the multiple bases;
      calculate, based on the volume data, two planes each being parallel to the base plane;
      calculate, based on the calculated two planes, a recommended region between the two planes for placing a balloon of a balloon catheter;

control operation of the X-ray irradiation device and the X-ray detection device and perform X-ray radiography of the region including the branch artery; and align and display the region including the branch artery, the calculated recommended region, and a balloon image on each of a plurality of X-ray images displayed as moving images, the balloon image representing the balloon as inflated, the X-ray images being based on the detected X-rays.

9. The X-ray radiographic apparatus according to claim 8, wherein the processing circuitry is configured to display a forefront position of the balloon and orientation of the balloon so as to match a forefront position of a catheter region and an orientation of the catheter region on the X-ray image, respectively, the forefront position of the balloon being based on the balloon volume and the orientation of the balloon being defined as a direction from a rear end position to the forefront position.

10. The X-ray radiographic apparatus according to claim 9, wherein the processing circuitry is configured to determine the orientation of the balloon from a trajectory of the forefront position of the catheter region on the X-ray image.

11. The X-ray radiographic apparatus according to claim 10, wherein the processing circuitry is configured to regard a direction from the forefront position of the catheter region on a past X-ray image to the forefront position of the catheter region on a current X-ray image as current orientation of the balloon.

12. The X-ray radiographic apparatus according to claim 8, wherein the processing circuitry is configured to calculate the base based on the region including the branch artery as well as on the centerline.

13. The X-ray radiographic apparatus according to claim 8, wherein the processing circuitry is configured to:

determine whether or not a forefront position of the catheter on the aligned image goes beyond the recommended region;

mark the aligned image for warning if it is determined that the forefront position of the catheter goes beyond the recommended region; and display the aligned image if it is determined that the forefront position of the catheter does not go beyond the recommended region, and display the aligned image by marking the aligned image for warning if it is determined that the forefront position of the catheter goes beyond the recommended region.

14. The X-ray radiographic apparatus according to claim 8, wherein the processing circuitry is configured to:

calculate the base of at least one of a brachiocephalic trunk, a left common carotid artery, and a left subclavian artery as the base of the branch artery; and calculate the recommended region based on the volume data and on the base of at least one of the branch arteries.

* * * * *